United States Patent [19]

van Aller et al.

[11] 4,398,937

[45] Aug. 16, 1983

[54] SELECTIVE ALGAECIDES FOR CONTROL OF CYANOCHLORONTA

[75] Inventors: Robert T. van Aller; George F. Pessoney, both of Hattiesburg, Miss.

[73] Assignee: The University of Southern Mississippi, Hattiesburg, Miss.

[21] Appl. No.: 308,987

[22] Filed: Oct. 6, 1981

[51] Int. Cl.³ .................... A01N 37/02; A01N 37/06
[52] U.S. Cl. .......................................... 71/67; 71/66; 71/88; 71/113; 71/79; 119/3; 210/764
[58] Field of Search ................ 7/67, 113, 66; 424/318

[56] References Cited

U.S. PATENT DOCUMENTS

| | | | |
|---|---|---|---|
| 1,767,041 | 6/1930 | Billing | 424/318 |
| 2,400,863 | 5/1946 | Gelfand | 71/67 |
| 3,148,049 | 9/1964 | Herschler | 71/113 |
| 3,247,054 | 4/1966 | Hodge | 71/67 |
| 3,514,278 | 5/1970 | Brink, Jr. | 71/67 |
| 3,684,477 | 8/1972 | Blumbergs et al. | 71/67 |
| 3,807,983 | 4/1974 | Abramitis | 71/67 |
| 3,874,869 | 4/1975 | Koppensteiner et al. | 71/86 |
| 4,336,054 | 6/1982 | Sjoerdsma | 71/67 |

FOREIGN PATENT DOCUMENTS

| | | | |
|---|---|---|---|
| 8061 | 7/1979 | European Pat. Off. | 71/67 |
| 76578 | 5/1970 | Fed. Rep. of Germany | 424/318 |
| 46-18153 | 5/1971 | Japan | 71/67 |
| 50-117923 | 9/1975 | Japan | 71/67 |
| 7202850 | 9/1972 | Netherlands | 71/88 |

OTHER PUBLICATIONS

Greenway et al., "Mechanism of the, etc.;" (1979) CA 92, No. 141,112z. (1980).
Kabara et al., "Fatty Acids and Derivatives, etc.;" (1972) CA 77, No. 122528p. (1972).
McGrattan et al., "Inhibition of Chlorella, etc.;" (1976) CA 84, No. 174489v. (1976).
Lillaram, "Soil Ioxins and Their Effect, etc;" (1970) CA 76, No. 817v. (1972).
Gloyna et al., "Suppression of Photosynthetic, etc.;" (1967) CA 66, No. 108052v. (1967).

*Primary Examiner*—Glennon H. Hollrah
*Attorney, Agent, or Firm*—C. Emmett Pugh

[57] ABSTRACT

This invention relates to the selective control of algae in ponds, sewage lagoons, cooling towers, lakes, and other bodies of water, including managed bodies of water, and deals particularly with the use of certain long-chain fatty acids and salts thereof for chemical control of Cyanochloronta (blue-green algae). Stimulation of Chlorophycophyta (green algae) is achieved by the use of one embodiment of this invention.

Application of the invention to bodies of water used in aquaculture eliminates earthy, musty flavors and other disagreeable flavors associated with blue-green algae in fish and other cultured organisms. Furthermore, a more balanced diversity of planktonic organisms can be maintained which makes oxygen depletion problems more manageable.

10 Claims, No Drawings

SELECTIVE ALGAECIDES FOR CONTROL OF CYANOCHLORONTA

TECHNICAL FIELD

This invention relates to the selective control of algae in ponds, sewage lagoons, cooling towers, lakes, and other bodies of water, including managed bodies of water, and deals particularly with the use of certain long-chain fatty acids and salts thereof for chemical control of Cyanochloronta (blue-green algae). Stimulation of Chlorophycophyta (green algae) is achieved by the use of one embodiment of this invention.

Application of the invention to bodies of water used in aquaculture eliminates earthy, musty flavors and other disagreeable flavors associated with blue-green algae in fish and other cultured organisms. Furthermore, a more balanced diversity of planktonic organisms can be maintained which makes oxygen depletion problems more manageable.

BACKGROUND ART

Numerous chemical agents are known to control (i.e. kill or inhibit) blue-green algae growth, but each agent has disadvantages which limit its usage. For example, there are many potent algaecides which cannot be used because at useful concentrations they are extremely toxic to fish and other beneficial organisms. Other agents are known which have limited utility because of their high cost. Thus, there exists the need for improved means to effectively control undesirable blue-green algae existing in ponds, lakes, streams, etc.

It is, of course, desirable that algicides act quickly and fast action also aids to avoid loss by chemical degradation as well as diffusion due to water currents and/or weather conditions. It is also desirable that these algaecides not persist in the environment for long periods of time.

DISCLOSURE OF INVENTION

It has been found in accordance with this invention that blue-green algae can be effectively controlled by use, at low concentrations, of certain fatty acids having from 12 to 20 carbon atoms, branched or unbranched. Such fatty acids may advantageously have additional oxygen present as a radical such as hydroxyl, ketone or epoxy, singly or in combination. There may also be one or more unsaturated carbon bonds present in the fatty acids. Water soluble salts of the fatty acids such as sodium, potassium and the like are also advantageous blue-green algae control agents.

The present method of controlling the growth of blue-green algae in an aqueous medium advantageously comprises adding to the aqueous medium in an amount of from about 0.1 to about 100 ppm of said aqueous medium a fatty acid compound having from twelve to twenty carbon atoms. Preferably the fatty acid additionally has oxygen present as a radical selected from the group consisting of hydroxyl, ketone, epoxy and hydroperoxy. Additionally the carbon atoms present may be in branched form. Preferably the fatty acids are in the form of a water soluble salt selected from the group consisting of sodium salts and potassium salts.

Advantageously the fatty acid is a compound of the formula:

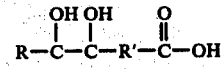

where:
R is an alkyl radical of from 1 to 16 carbon atoms,
R' is an alkyl radical of from 1 to 16 carbon atoms, and
the total of R and R' is from 9 to 17. Advantageously R is 8 and R' is 7 and the fatty acid is 9,10 dihydroxysteoric acid.

Advantageous results are also achieved when the fatty acid is a compound of the formula:

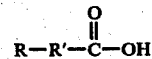

where:
R is an alkyl radical of from 1 to 17 carbon atoms,
R' contains at least one unsaturated carbon bond and from 2 to 18 carbon atoms, and
the total of R+R' is from 11 to 19. Preferable results are obtained when R is 5, and R' is 12 and R' contains two unsaturated carbon bonds. Advantageously the fatty acid is linoleic acid.

Advantageous results are obtained when the fatty acid is a compound of the formula:

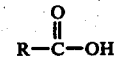

where:
R is an alkyl radical of from 11 to 19 carbon atoms. Preferably R is 11 and the fatty acid is dodecanoic acid.

Advantageous results are also achieved when the fatty acid is a compound of the formula:

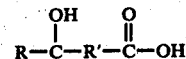

where:
R is an alkyl radical of from 1 to 16 carbon atoms,
R' contains at least one unsaturdated carbon bond and from 2 to 17 carbon atoms and
the total of R+R' is from 10 to 18, and in addition said fatty acid stimulates any green algae present in the aqueous medium. Preferable results are achieved when R is 7, and R' is 9 and the fatty acid is ricinoleic acid.

The compounds described above act as contact poisons and for this reason, blue-green algae control is achieved quickly and simply by treating the area with sufficient material to maintain a given strength of active ingredient in the water. The activity of the above described compounds is so high that satisfactory control can be obtained with a concentration as low as about 0.01 part per million of active ingredient in solution in the water. For most applications where an entire area such as a pond or lake is treated, concentrations of about 0.01 to 100 p.p.m. will be quite effective with no harm to fish or other aquatic organisms. The preferred concentration range which will usually be from about 0.1 to about 10 p.p.m. The lower range of concentrations from 0.1 ppm to 2 ppm may be used to prevent the growth of blue-green algae and to maintain proper plankton diversity, whereas the higher concentrations of 1 to 100 ppm may be used to kill and remove blue-green algae from the water column.

The manner in which the water area may be treated will vary with the specific problems encountered. Since the active ingredient is water soluble it will diffuse out from the area treated. However, in this invention is not serious because of the very fast action of the agents. In treating small areas where the problem is usually critical around the edge of the pond it is more practical to treat the marginal area from the bank than to treat from the center. Furthermore, because of the diffusion of the agents toward the center in static water, control will be obtained there also. Although aqueous solutions are usually preferred for economic reasons, solutions of the salts in other solvents may be used and such solutions used for the water treatment.

Treatment is accomplished best by spraying on the water or by injection just below the water surface with distribution as evenly as possible in the area to be treated. Spraying equipment is preferably used with aqueous solutions and because the agent is applied as an aqueous solution no problem of preparation, operation or cleaning is involved. In general, the diluted treating solution will contain about 10% to about 50% by weight of active ingredient. Although the product is water soluble at the concentrations used, it may frequently be desirable to incorporate a small amount of a dispersant as a mixing aid in the initial concentrate used to prepare the diluted treating solutions. For this purpose, isopropyl alcohol, diacetone alcohol or other water soluble alcohols or ketones may be used. Where a dispersant is used the formulated concentrate will usually contain from about 15% to 30% of the dispersing agent.

In addition to treating the area with a solution by a spraying technique the treating agents may also be formulated in a granular form and applied by any of the variety of manual, electrical and gas-powered whirling spreaders on the market and which can be adapted for use on boats. This granular formulation consists of an approximately 1% to 10% (preferably about 5%) concentration of active agent deposited on, any inert material such as Attapulgite, Bentonite and other inert adsorbent granulated clays having a size range of about 8 to 30 mesh (U.S. sieve size).

The granular formulations can be prepared simply by spraying the liquid active ingredient or concentrates thereof into the granular inert carrier in a rotating or other suitable blender common to the trade for preparation of formulations. Although the granulated formulations can be prepared containing from 1 to 25% of active ingredient it has been found that 5% of the active ingredient is generally the best concentration to use for obtaining good distribution when the formulation is applied. To treat one acre of water surface with a 5% by weight granular formulation at a level of one part per million of active agent will require 240 pounds of the granular material for each foot of pond depth. Since again the depth of pond and the dose concentration are directly proportional, the amount of granular material for other depths and at other concentrations may be readily calculated. Use of a granular formulation is advantageous for control of submerged algae since the granular agent sinks to the bottom of the pond.

As indicated, the active agents described above are effective in accord with this invention for the selective control of algae in aquatic systems. One of the particular advantages of the invention is that it enables specific algae, blue-green algae, to be controlled with a single active ingredient, which is essentially bio-degradable.

In addition to use in ponds and lakes, this invention is applicable to the control of blue-green algae in mariculture systems, aquaculture systems, sewage treatment systems and other eutropic systems. Catfish production ponds and sewage lagoons are particularly suited for treatment by this invention.

BEST MODE FOR CARRYING OUT THE INVENTION

In order to more fully describe and illustrate the invention, the following examples are given:

The algae used in this particular study were Chlamydomonas sp., *Chlorella vulgaris*, Anabaena sp., and *Anabaena flos-aquae*. Cultures of these algae were obtained, subcultured, and aqueous stocks of algae in 400 ml BBM were prepared and were used in log phase growth to innoculate test cultures.

The fatty acids which were tested as algal inhibitors were 9, 10-dihydroxystearic acid, linoleic acid, dodecanoic acid, and ricinoleic acid.

The test procedure involved placing 15 ml of BBM into 25 ml test tubes and innoculating them with 0.2 ml of algal stock solution. Twenty test tubes were innoculated with each algae. Four of these cultures were used with each concentration of each of the fatty acids. Four tubes from each set served as controls. Four concentrations of the fatty acids were used for each alga. The concentrations studied were 0.5 PPM, 1.0 PPM, 5.0 PPM, and 10.0 PPM.

Algal cultures were incubated under constant light of about 200 foot-candles and at a temperature of 68° F. Bold's Basal Medium (BBM), a modification of Bristol's solution was the medium in which all the cultures were grown. Bold's Basal Medium was prepared as follows:

To each of six 400 ml stock solutions of distilled water one of the following chemicals was added in the appropriate amount:

| | |
|---|---|
| $NaNO_3$ | 10.0 g |
| $CaCl_2$ | 1.0 g |
| $MgSO_4.7H_2O$ | 2.0 g |
| $KH_2PO_4$ | 6.0 g |
| $K_2HPO_4$ | 4.0 g |
| NaCl | 1.0 g |

To 940 ml of glass-distilled water were added 10 ml of each stock solution of 1 ml of each of the following stock trace element solutions:

| | | | |
|---|---|---|---|
| I. | EDTA stock solution | EDTA | 50.0 g |
| | | KOH, 85% | 31.0 g |
| | | DIST. $H_2O$ | to 1000 ml |
| II. | H—Fe stock solution | $FeSO_4 7H_2O$ | 4.98 g |
| | | Acidified DIST. $H_2O$ to 1000 ml (1.0 ml conc. $H_2SO_4$ plus 99, 109 ml DIST. $H_2O$) | |
| III. | Boron stock solution | $H_3BO_3$ | 11.42 g |
| | | DIST. $H_2O$ | to 1000 ml |
| IV. | H—H5 stock solution | $ZnSO_4$ | 8.82 g |
| | | $MnCl_2$ | 1.44 g |
| | | $MoO_3$ | 0.71 g |
| | | $CuSO_4.5H_2O$ | 1.57 g |
| | | $Co(NO_3)_2.6H_2O$ | 0.49 g |
| | | Acidified | to 1000 ml ml DIST. |

| | |
|---|---|
| | H₂O |

Concentrations of fatty acids and the amount of stock solution used to prepare them were as follows:

| | |
|---|---|
| 0.5 PPM | 0.05 ml of stock solution at 150 PPM |
| 1.0 PPM | 0.1 ml of stock solution at 150 PPM |
| 5.0 PPM | 0.5 ml of stock solution at 150 PPM |
| 10.0 PPM | 1.0 ml of stock solution at 150 PPM |

Each test tube contained 15 ml sterile BBM. To this was added an aliquot of 0.2 of algal stock solution. Then the appropriate aliquots of warm acid stock solution were added to the appropriate number of culture tubes. These cultures were then incubated 5 days and at that point were counted. The same cultures were also counted after a 12 day growth period.

Stock solutions of the fatty acids to be tested as algal inhibitors were made from a stock solution of 5% sodium bicarbonate in glass-distilled water. The 5% sodium bicarbonate stock solution was made by dissolving 150 grams of sodium bicarbonate in 3000 ml of glass-distilled water. To insure complete dissolution, the solution was heated and stirred on a magnetic stirrer hot plate. The warm solution was used in preparing the fatty acid stock solutions.

9,10-Dihydroxystearic Acid

Thirty mg of 9,10-dihydroxystearic acid was dissolved in 200 ml of the 5% sodium hydroxide solution to produce a stock solution of 9,10-dihydroxstearic acid.

Linoleic Acid

Twenty-five mg of linoleic acid was dissolved in 166.5 ml of 5% sodium bicarbonate solution to produce a stock solution of linoleic acid.

Dodecanoic Acid

Twenty-five mg of dodecanoic acid was dissolved in 166.5 ml of 5% sodium bicarbonate solution to produce a solution of the acid.

Ricinoleic Acid

One hundred mg of ricinoleic acid was dissolved in 666.5 ml of 5% sodium bicarbonate solution to produce a stock solution of the acid.

Quanitative phytoplankton values were determined using the random field method. Filaments, colonies, and aggregations of cells were recorded as algal units. Each unit consisted of approximately 6 cells. Unicellular algae were counted as separate units. Algal counts were made from each of three duplicate cultures. One ml of the algal sample was placed in a Sedgwick-Rafter counting chamber, which is 50 mm long by 20 mm, wide by 1 mm deep. A Wild Heerbrugg, compound microscope with a Whipple grid eyepiece was used to determine quantitative algae values.

One ml of the algal solution was placed in the counting chamber, and two drops of methyl cellulose were added to minimize the movement of Chlamydomonas sp. Ten random fields were counted and all organisms within the Whipple grid field were enumerated.

The following formula used to calculate the numbers per milliliter from the field counts:

$$No/ml = \frac{C \times 1000 \text{ mm}^3}{A \times D \times F}$$

where:
C = number of organisms counted,
A = area of a field (Whipple grid immage area), mm²,
D = depth of a field (S-R cell depth), mm, and
F = number of fields counted The area of the Whipple grid used was 0.46 mm², and the depth of a field was 1 mm. Results of the counts were reported as algal units/ml.

Counts of algae at 5 and 12 days showed that the fatty acids had an effect on at least some of the algae. Effects were easily recognizable, showing typical patterns of stimulation, inhibition, or ineffectiveness. Two species of Anabaena were considered to demonstrate whether species differences had any role in blue-green inhibition. Different species of green algae were used to demonstrate whether blue-green algae were selectively inhibited by fatty acids.

Anabaena sp.

Ricinoleic acid was effective in inhibiting Anabaena sp. after 5 days, showing a reduction in algal units/ml of 9,783, or 30.6% of the control at a concentration of 10.0 PPM (Table I). Ricinoleic acid also showed a stimulatory effect in concentrations of 1.0 PPM or less. 9,10-dihydroxystearic acid was also effective as a inhibitor at 5 days, showing a reduction in algal units/ml of the control at 10.0 PPM. It was less effective after 12 days, showing only a 16.6% reduction of the control. The least effective fatty acid was dodecanic acid, which reduced the algal units/ml of the control by only 22.7% at 10.0 PPM. Dodecanic acid was slightly more effective at 12 days, showing a 22.7% reduction of the control at 10 PPM. Linoleic acid was the most effective fatty acid at 10.0 PPM after 5 days, showing a reduction of algal units/ml of 12,174 or 38.1% of the control. It was less effective at 12 days, showing only a 19.5% reduction of algal units/ml at 10 PPM. Ricinoleic was the most effective fatty acid at 10 PPM at 12 days, showing a reduction of algal units/ml of 76,956 or 65.2% of the control. In addition it was most effective acid at 5.0 PPM after 5 days with a 15.6% reduction of the number of algal units/ml of the control, and after 12 days ricinoleic acid showed a reduction of algal units/ml of 70,434 or 59.7% of the control at 0.5 PPM.

The cultures of *Anabaena flos-aquae* were less concentrated than the unidentified species after 5 days (Table II). They were more concentrated after 12 days. Still, 9,10-dihydroxystearic acid and linoleic acid indicated an inhibitory effect at 5 days at 10 PPM. Both reduced the algal units/ml of the control by 90.9%. Algal growth was stimulated by 9,10-dihydroxystearic acid at concentrations of 1.0 PPM and less. Linoleic acid, which showed stimulation at 1.0 PPM but inhibition at 0.5 PPM. Both acids produced an inhibitory effect at all concentrations after 12 days. Dodecanoic acid was the least effective fatty acid at both 5 and 12 days. It showed some inhibitory effects at all concentrations but the percentage of inhibition was less than that produced by the other acids. Ricinoleic acid demonstrated an inhibitory effect at all concentrations at both 5 and 12 days. While about as effective as linoleic acid or 9,10-dihydroxystearic acid at 5 days at 10 PPM, it was usually more effective than they were at the lower concentrations (Table II). And at 12 days at 10 PPM it was the most effective, showing a reduction in the number of algal units/ml of 38,261 or 92.6% of the control. *Chlorella vulgaris* was not inhibited by any of the 4 fatty acids (Table III). Although there was slight variation in the numbers of algal units/ml between the control and the other cultures, the variation was small. The only variation was demonstrated by ricinoleic acid at all concentrations at 5 days and at the 5 and 10 PPM concentrations at 12 days. In both cases ricinoleic demonstrated a stimulatory effect. For instance, at 5 days at 0.5 PPM there were 86.0% more algal units/ml than in the control. And at 12 days at 10 PPM there were 50.0% more algal units/ml than in the control.

Chlamydomonas sp.

The cultures of Chylamydomonas sp. were mostly unaffected by any of the four fatty acids (Table IV). However, both linoleic acid and 9,10-dihydroxystearic acid showed an inhibitory effect at 10 PPM after 5 days. Both reduced the number of algal units/ml by 5,000 or 43.4% of the control. None of the 4 fatty acids demonstrated an inhibitory effect at 12 days. But ricinoleic acid, as in the *Chlorella vulgaris* cultures, did exhibit a stimulatory effect after 5 and 12 days at all concentrations. At 5 days the maximum stimulatory effect took place at 5.0 PPM with a 183.0% increase in the number of algal units/ml of the control. At 12 days the maximum stimulatory effect exhibited a ricinoleic acid occurred at 0.5 PPM.

In addition to the counts at 5 days and 12 days, the cultures were observed visually for several more weeks. After 19 days, the cultures of both species of Anabaena appeared to die almost completely where acids were present. The controls appeared healthy for 5 or 6 more weeks. All cultures of Chlamydomonas sp. and *Chlorella vulgaris* appeared to stay healthy for 7 or 8 weeks after the 12 day count was made.

As a means of visually confirming some of the results batch cultures of 300 ml. of *Anabaena flos-aquae* and *Chlorella vulgaris* were grown. For each alga there was one control, two cultures at 10.0 PPM concentrations of ricinoleic acid, which seemed to be the most effective blue-green algal inhibitor in the test tube cultures. All cultures of *Chlorella vulgaris* grew well and no inhibition was noticed. *Anabaena flos-aquae* seemed to be slightly inhibited at 1 PPM and greatly inhibited at 10 PPM.

TABLE I

ALGAL UNITS/ML OF ANABAENA sp. AT 5 AND 12 DAY INTERVALS GROWN IN BOLD'S BASAL MEDIUM WITH SELECTED CONCENTRATIONS OF 4 FATTY ACIDS

| Control | | | | |
|---|---|---|---|---|
| Units/ml 5 days | 31957 | | | |
| Units/ml 10 days | 118043 | | | |
| 9,10-Dihydroxystearic Acid | | | | |
| Concentrations | 0.5 PPM | 1.0 PPM | 5.0 PPM | 10.0 PPM |
| Units/ml 5 days | 34130 | 38043 | 30217 | 23261 |
| Units/ml 12 days | 158043 | 166739 | 106957 | 98473 |
| Linoleic Acid | | | | |
| Concentrations | 0.5 PPM | 1.0 PPM | 5.0 PPM | 10.0 PPM |
| Units/ml 5 days | 45217 | 46957 | 32609 | 19783 |
| Units/ml 12 days | 114565 | 135217 | 98261 | 95000 |
| Dodecanoic Acid | | | | |
| Concentrations | 0.5 PPM | 1.0 PPM | 5.0 PPM | 10.0 PPM |
| Units/ml 5 days | 40435 | 32609 | 28261 | 28696 |
| Units/ml 12 days | 139348 | 135217 | 92826 | 91204 |
| Ricinoleic Acid | | | | |
| Concentrations | 0.5 PPM | 1.0 PPM | 5.0 PPM | 10.0 PPM |
| Units/ml 5 days | 36522 | 35652 | 26957 | 22174 |
| Units/ml 12 days | 97391 | 81957 | 47609 | 41087 |

TABLE II

ALGAL UNITS/ML OF ANABAENA flos-aquae AT 5 and 12 DAY INTERVALS GROWN IN BOLD'S BASAL MEDIUM WITH SELECTED CONCENTRATIONS OF 4 FATTY ACIDS

| Control | | | | |
|---|---|---|---|---|
| Units/ml 5 days | 2391 | | | |
| Units/ml 12 days | 41304 | | | |
| 9,10-Dihydroxystearic Acid | | | | |
| Concentrations | 0.5 PPM | 1.0 PPM | 5.0 PPM | 10.0 PPM |
| Units/ml 5 days | 4348 | 4348 | 2174 | 217 |
| Units/ml 12 days | 18478 | 13478 | 9130 | 3261 |
| Linoleic Acid | | | | |
| Concentrations | 0.5 PPM | 1.0 PPM | 5.0 PPM | 10.0 PPM |
| Units/ml 5 days | 1087 | 3261 | 1087 | 217 |
| Units/ml 12 days | 14565 | 8261 | 4130 | 3969 |
| Dodecanoic Acid | | | | |
| Concentrations | 0.5 PPM | 1.0 PPM | 5.0 PPM | 10.0 PPM |
| Units/ml 5 days | 1087 | 2174 | 2714 | 2174 |
| Units/ml 12 days | 20435 | 7609 | 6739 | 6522 |
| Ricinoleic Acid | | | | |
| Concentrations | 0.5 PPM | 1.0 PPM | 5.0 PPM | 10.0 PPM |
| Units/ml 5 days | 435 | 1087 | 1087 | 652 |
| Units/ml 12 days | 10217 | 6522 | 4783 | 3043 |

TABLE III

ALGAL UNITS/ML OF CHLORELLA vulgaris AT 5 AND 12 DAY INTERVALS GROWN IN BOLD'S BASAL MEDIUM WITH SELECTED CONCENTRATIONS OF 4 FATTY ACIDS

| Control | | | | |
|---|---|---|---|---|
| Units/ml 5 days | 10870 | | | |
| Units/ml 12 days | 217391 | | | |
| 9,10-Dihydroxystearic Acid | | | | |
| Concentrations | 0.5 PPM | 1.0 PPM | 5.0 PPM | 10.0 PPM |
| Units/ml 5 days | 11304 | 12609 | 11087 | 10652 |
| Units/ml 12 days | 217391 | 217391 | 217391 | 217391 |
| Linoleic Acid | | | | |
| Concentrations | 0.5 PPM | 1.0 PPM | 5.0 PPM | 10.0 PPM |
| Units/ml 5 days | 8697 | 12174 | 10870 | 11304 |
| Units/ml 12 days | 195652 | 239130 | 304348 | 195652 |
| Dodecanoic Acid | | | | |
| Concentrations | 0.5 PPM | 1.0 PPM | 5.0 PPM | 10.0 PPM |
| Units/ml 5 days | 8913 | 11304 | 11304 | 10435 |
| Units/ml 12 days | 217391 | 217391 | 217391 | 217391 |
| Ricinoleic Acid | | | | |
| Concentrations | 0.5 PPM | 1.0 PPM | 5.0 PPM | 10.0 PPM |
| Units/ml 5 days | 20217 | 21739 | 22391 | 20870 |
| Units/ml 12 days | 217391 | 326087 | 326087 | 326087 |

TABLE IV

ALGAL UNITS/ML OF CHLAMYDOMONAS sp. AT 5 AND 12 DAY INTERVALS GROWN IN BOLD'S BASAL MEDIUM WITH SELECTED CONCENTRATIONS OF 4 FATTY ACIDS

| Control | | | | |
|---|---|---|---|---|
| Units/ml 5 days | 11522 | | | |
| Units/ml 12 days | 48696 | | | |
| 9,10-Dihydroxystearic Acid | | | | |
| Concentrations | 0.5 PPM | 1.0 PPM | 5.0 PPM | 10.0 PPM |
| Units/ml 5 days | 10217 | 10436 | 11304 | 6522 |
| Units/ml 12 days | 47826 | 46739 | 50000 | 53478 |
| Linoleic Acid | | | | |
| Concentrations | 0.5 PPM | 1.0 PPM | 5.0 PPM | 10.0 PPM |
| Units/ml 5 days | 11087 | 12609 | 12391 | 6522 |

TABLE IV-continued

ALGAL UNITS/ML OF CHLAMYDOMONAS sp. AT 5 AND 12 DAY INTERVALS GROWN IN BOLD'S BASAL MEDIUM WITH SELECTED CONCENTRATIONS OF 4 FATTY ACIDS

| | | | | |
|---|---|---|---|---|
| Units/ml 12 days | 45652 | 52174 | 50000 | 51087 |
| Dodecanoic Acid | | | | |
| Concentrations | 0.5 PPM | 1.0 PPM | 5.0 PPM | 10.0 PPM |
| Units/ml 5 days | 10652 | 10435 | 12609 | 11957 |
| Units/ml 12 days | 47174 | 48696 | 46304 | 50217 |
| Ricinoleic Acid | | | | |
| Concentrations | 0.5 PPM | 1.0 PPM | 5.0 PPM | 10.0 PPM |
| Units/ml 5 days | 18696 | 29130 | 32609 | 13043 |
| Units/ml 12 days | 65217 | 63043 | 52174 | 54348 |

Another laboratory experiment was run to further substantiate the selective effect of one of the algaecides, potassium ricinoleate. Two species of blue-green algae, Lyngbya and Cylindrospermum, and three species of green algae, Chlorella, Haematococcus and Stigeoclonium and Tribonema, a yellow-green alga of the division Chrysophycophyta, were treated as follows: Twenty ml test tubes of sterile BBM culture solution were innoculated with each alga. All species of algae were evaluated with three groups, control, 2.5 ppm algaecide and 7.5 ppm algaecide. Each group was run with triplicate samples.

Controls were counted 6 days after innoculation, algaecide was added to the treatment groups seven days after innoculation and all test tubes were counted thirteen days after innoculation. The results are shown in Table V. After seven days, there was a 31% reduction in the Lyngbya cultures at 2.5 ppm algaecide and a 40% reduction at 7.5 ppm. After seven days, there was a 60% reduction in Cylindrospermum cultures at 2.5 ppm algaecide and a 72% reduction at 7.5 ppm. Chlorella was slightly inhibited, Haematococcus was stimulated and Stigeoclonium remained unchanged. The reduction in cell numbers of Tribonema were similar to those determined for the blue-green algae. After thirteen days, there was a 55% reduction in numbers at both 2.5 ppm and 7.5 ppm. After twenty days there was a 27% reduction at both concentrations. These results with Tribonema are particularly important since comparisons of algal components in bodies of water having taste and odor problems often show the presence of Chrysophycophyta as a prevalent division of algae during the cooler months. They are, like blue-green algae, often associated with taste and odor problems.

TABLE V

SELECTIVE EFFECTS OF POTASSIUM RICINOLEATE ON GREEN, BLUE-GREEN, AND YELLOW-GREEN ALGAE.

| Algae | days[a] | control cells/ml[b] | 2.5 ppm cells/ml[b] | 7.5 ppm cells/ml[b] |
|---|---|---|---|---|
| Lyngbya | 6 | 1462 | — | — |
| | 13 | 3375 | 2340 | 2010 |
| Cylindospermum | 6 | 6100 | — | — |
| | 13 | 6300 | 2500 | 1770 |
| Chlorella | 6 | 6400 | — | — |
| | 13 | 61000 | 44000 | 49000 |
| Haematococcus | 6 | 4200 | — | — |
| | 13 | | 39000 | 23000 | 52000 |
| Stigeoclonium | 6 | 1620 | — | — |
| | 13 | 2000 | 1900 | 1900 |
| Tribonema | 6 | 489 | — | — |
| | 13 | 13035 | 5885 | 5335 |
| | 20 | 14300 | 10510 | 10295 |

[a]days after innoculation
[b]average of 3 samples by random field method

Field Tests

A series of field tests were completed using potassium ricinoleate because growth conditions are different in large ponds as compared to laboratory conditions. Field Experiment I to determine effectiveness of potassium ricinoleate in controlling blue-green algae in catfish ponds was conducted during the period from Mar. 1, 1980, to Mar. 19, 1981. Plankton samples were taken periodically during this period from twenty-two ponds at two different locations. Numbers of net plankton were enumerated as with the laboratory tests. A two surface acre pond containing juvenile channel catfish was dedicated for experimental treatment and the other twenty-one served as controls. The experimental pond historically had produced dense blooms of blue-green algae during the warm months and usually produced fish having an earthy, musty taste and odor. In addition to plankton numbers in samples from the experimental pond, total organism dry weight and chlorophyll a values were determined.

On July 30, 1980, most ponds had numbers of blue-green algae exceeding $2 \times 10^6$ cells/liter. These algae were predominantly Oscillatoria, Microcystis and Anacystis with smaller numbers of Nostoc, Anabaena and Lyngbya. The experimental pond had $1.2 \times 10^6$ cells/liter composed mainly of Microcystis sp. Large numbers of copepods and rotifers were present. On July 30, the pond was treated with 10 ppm potassium ricinoleate by distributing a 30% aqueous solution evenly through the water column by pump from a small boat. Before and after treatment data are shown in Table VI. Samples taken seven days after treatment show that 93% of the blue-green algae were killed. Numbers of zooplankton and other phytoplankton were essentially unchanged or increased in numbers which again demonstrated the selective effects of the algaecide. This is further substantiated by the dry weights and chlorophyll a levels.

Furthermore, this condition prevailed until Sept. 6, 1980, when Oscillatoria began to increase in numbers. Control ponds continued to have numbers of blue-green cells in excess of $2 \times 10^6$ per liter until cool weather in October. Juvenile catfish fed and otherwise appeared healthy in the experimental pond. Samples of fish were taken in February, 1981 and monthly from February through June, 1981 and cooked to determine taste and odor. There were no taste or odor problems.

TABLE VI

EXPERIMENTAL POND TREATMENT I

| Dates | Cells/ Liter of G[a] | Cells/ Liter of Bg[b] | Zoo #/ Liter | Dry Wgts Gm/Liter | Chlor. a A[c] |
|---|---|---|---|---|---|
| June (mo/avg) | $1.3 \times 10^4$ | $1.2 \times 10^6$ | 4050 | 17.0 | .127 |
| July[d] (mo/avg) | $4.5 \times 10^4$ | $8.8 \times 10^5$ | 2700 | 7.67 | .264 |
| 7/30 Pre-treatment | $3.2 \times 10^4$ | $1.4 \times 10^6$ | 2025 | 16.85 | .484 |
| 7/31 Post treatment | $6.2 \times 10^4$ | $3.2 \times 10^5$ | 2531 | 2.19 | .000 |
| 8/1 Post-treatment | $5.0 \times 10^4$ | $1.8 \times 10^5$ | 2500 | 4.45 | .064 |
| 8/6 Post-treatment | $2.1 \times 10^4$ | $1.0 \times 10^5$ | 4050 | 17.90 | .000 |
| 8/19 Post treatment | 0 | $5.4 \times 10^5$ | 2025 | 5.34 | .002 |
| 9/6 Post-treatment | $1.7 \times 10^4$ | $3.8 \times 10^5$ | 4050 | 20.69 | .240 |
| 9/23 Post treatment | $4.5 \times 10^5$ | $1.9 \times 10^6$ | 506 | 9.06 | NA |
| 11/21[e] Post | | | | | |

TABLE VI-continued
EXPERIMENTAL POND TREATMENT I

| Dates | Cells/ Liter of G[a] | Cells/ Liter of Bg[b] | Zoo #/ Liter | Dry Wgts Gm/Liter | Chlor. a A[c] |
|---|---|---|---|---|---|
| treatment | $2.5 \times 10^3$ | 0 | 1012 | 1.03 | NA |
| 12/14 Post treatment | 0 | $3.0 \times 10^4$ | 1518 | 4.84 | NA |

[a]G — green algae
[b]Bg — blue-green algae
[c]A — absorbance at 663 nm
[d]pond volume reduced by 50% 7/5/81 and refilled 7/12/81
[e]normal winter reduction in all ponds
Zoo — Zooplankton
Chlor a — Chlorophyll a In Field Experiment II, a 10 acre catfish pond was monitored for plankton numbers as before and treated with potassium ricinoleate, one of the algaecides. This particular pond contained adult catfish that had a strong earthy, musty taste and odor in March, 1980 that persisted throughout the remainder of 1980 and the spring of 1981. Table VII shows that Oscillatoria and Microcystis, both blue-green algae, were the predominant algae during this period. A taste and odor scale of 0 to 5 was developed with a professional taste tester with 5 being the worst and 0 being undetectable. The pond was treated with 2 ppm potassium ricinoleate on May 26, 1981, at which time the pond contained in excess of $1 \times 10^6$ blue-green algae cells/liter. After two days, there were essentially no blue-green algae present. Green algae and zooplankton remained unchanged through June, 1981.

Table VIII shows that the earthy musty taste and odor were eliminated from the fish over a three week period. There were no oxygen depletion problems noted.

TABLE VII
EXPERIMENTAL POND TREATMENT II

| | Cells/ liter G[a] | Cells/ liter Bg[b] | Zoo #'s/ liter | Comments |
|---|---|---|---|---|
| March 80 | $1.3 \times 10^5$ | $1.4 \times 10^6$ | 2500 | Osc |
| 6/11/80 | $1.0 \times 10^5$ | $2.6 \times 10^5$ | 4500 | Osc & Mic |
| 7/24/80 | $8.1 \times 10^4$ | $2.3 \times 10^6$ | 1000 | Mic, Osc |
| 8/19/80 | $2.5 \times 10^4$ | $7.37 \times 10^6$ | 3500 | Mic, Osc, Nos |
| 9/5/80 | $5.6 \times 10^4$ | $8.94 \times 10^6$ | 1010 | Mic, Osc |
| 9/23/80 | $1.8 \times 10^5$ | $6.3 \times 10^6$ | 3040 | Mic |
| 1/23/81 | $1.8 \times 10^4$ | $4.4 \times 10^5$ | 1520 | Mic |
| 1/31/81 | $3.2 \times 10^4$ | $1.85 \times 10^5$ | 1520 | Mic |
| 3/26/81 | $7.7 \times 10^4$ | $9.7 \times 10^4$ | 6580 | Tri, Mic |
| 4/21/81 | $2.3 \times 10^4$ | $6.0 \times 10^4$ | 1520 | Osc, Tri, Ped |
| 5/7/81 | $7.4 \times 10^4$ | $4.1 \times 10^5$ | 3040 | Mic, Ped |
| 5/21/81 | $3.2 \times 10^5$ | $8.9 \times 10^5$ | 2280 | Mic, Ped |
| 5/26/81 A | $1.3 \times 10^5$ | $1.3 \times 10^6$ | 7600 | Pre-Treat: Mic, Osc |
| 5/26/81 B | $3.2 \times 10^5$ | $4.2 \times 10^5$ | 755 | Post-Treat: - 4 p.m. Mic, Deep |
| 5/26/81 C | $2.0 \times 10^5$ | 0 | 2270 | Post-Treat - 4 p.m. Ped, Shallow |
| 5/27/81 D | $2.6 \times 10^5$ | $1.18 \times 10^4$ | 0 | 9:40 p.m. - Ped, Deep |
| 5/27/81 E | $1.09 \times 10^5$ | 0 | 1510 | 9:40 p.m. - Ped, Shallow |
| 5/28/81 F | $1.3 \times 10^5$ | $5.9 \times 10^3$ | 756 | 7 a.m. - Ped |
| 5/28/81 G | $1.1 \times 10^5$ | 0 | 2270 | 11 a.m. - Ped |

[a]G — green algae
[b]Bg — blue-green algae
[c]Prevalent algae:
Osc — Oscillatoria
Mic — Microcystis
Nos — Nostoc
Tri — Tribonema
Ped — Pediastrum
Zoo — Zooplanton

TABLE VIII
TASTE AND ODOR IN EXPERIMENTAL POND II

| | Fish | | Water | |
|---|---|---|---|---|
| Date | Taste | Odor | Taste | Odor |
| 5/26/81 | 4 | 4 | 2 | 1 |
| 6/1/81 | 3 | 2 | 1 | 0 |
| 6/5/81 | 2 | 1 | 1 | 0 |
| 6/12/81 | 1 | 1 | 0 | 0 |
| 6/15/81 | 0 | 0 | 0 | 0 |

In Field Experiment III, a small two acre pond was monitored for a complete year for plankton organisms as before. Oscillatoria and Microcystis were usually the prevalent blue-green algae. On 6/9/81 the pond was experiencing a bloom consisting completely of Oscillatoria. Channel catfish from the ponds had the characteristic earthy, musty taste and odor of 4 and 4 respectively on the 0 to 5 scale. The pond was treated on this date with 2 ppm potassium ricinoleate, one of the selective algaecides, as before. The results are shown in Table IX. On June 22, the predominant alga was Pediastrum with isolated fragments of Oscillatoria filaments. Sample fish from this pond had lost all of the earthy, musty taste and odor by this date.

TABLE IX
EXPERIMENTAL POND TREATMENT III

| | Cells/ liter G[a] | Cells/ liter Bg[b] | Zoo #'s/ liter | Comments |
|---|---|---|---|---|
| 3/6/80 | $7.8 \times 10^4$ | 0 | 3026 | Tri, GUC |
| 6/10/80 | $2.7 \times 10^4$ | $6.4 \times 10^6$ | 1518 | Osc, Mic |
| 6/18/80 | $3.6 \times 10^3$ | $1.6 \times 10^6$ | 4149 | Osc, Mic |
| 7/24/80 | $5.2 \times 10^4$ | $2.3 \times 10^6$ | 1991 | Osc, Mic |
| 8/19/80 | $1.1 \times 10^4$ | $3.8 \times 10^6$ | 5098 | Osc, Mic, Art |
| 9/6/80 | 0 | $1.5 \times 10^6$ | 648 | Osc, Art |
| 9/23/80 | $5.5 \times 10^3$ | $2.7 \times 10^6$ | 3037 | Mic, Osc |
| 11/21/80 | $1.2 \times 10^5$ | $3.0 \times 10^4$ | 506 | Ulo, Osc |
| 12/14/80 | $3.7 \times 10^4$ | $2.6 \times 10^5$ | 1013 | Osc, Mic |
| 2/19/81 | $3.9 \times 10^4$ | $2.5 \times 10^5$ | 4556 | Mic, Ped |
| 3/26/81 | $2.8 \times 10^4$ | 0 | 506 | GUC |
| 4/21/81 | $9.0 \times 10^4$ | $6.4 \times 10^5$ | 1818 | Mic, Ped |
| 5/7/81 | $1.6 \times 10^5$ | $1.2 \times 10^6$ | 3784 | Mic, Osc, Ped, GUC |
| 5/26/81 | $2.0 \times 10^4$ | $1.1 \times 10^6$ | 2054 | Osc, Ped |
| 6/9/81 | $1.3 \times 10^4$ | $2.5 \times 10^6$ | 746 | Pre-treat - Osc |
| 6/10/81 | $3.0 \times 10^3$ | $2.8 \times 10^6$ | 2251 | Osc, Mic |
| 6/12/81 | $1.4 \times 10^3$ | $1.3 \times 10^6$ | 4948 | Osc |

TABLE IX-continued
EXPERIMENTAL POND TREATMENT III

| | Cells/ liter G[a] | Cells/ liter Bg[b] | Zoo #'s/ liter | Comments |
|---|---|---|---|---|
| 6/22/81 | 3.5 × 10⁵ | 1.2 × 10⁴ | 4541 | Ped |

[a]G — green algae
[b]Bg — blue-green algae
[c]Prevalent algae
Art — Arthrospira
GUC — Unidentified green unicellular alga
Mic — Microcystis
Osc — Oscillatoria
Ped — Pediastrum
Tri — Tribonema
Ulo — Ulothrix
Zoo — Zooplanton

Sewage Treatment Tests

Two experiments were performed on sewage to further illustrate the utility of these algaecides. In the first experiment, sewage containing mostly green algae was treated with relatively high concentrations of potassium ricinoleate. The results after six days of aeration are shown below:

| | |
|---|---|
| control | 2.15 × 10⁵ cells/liter |
| 18.4 ppm | 1.91 × 10⁵ cells/liter |
| 46.0 ppm | 1.33 × 10⁵ cells/liter |
| 92.0 ppm | 2.30 × 10⁵ cells/liter |
| 184.1 ppm | 2.72 × 10⁵ cells/liter |

Genera present before treatment were:
Actinastrum
Closterium
Rhizochrysis
Ankistrodesum
Selenastrum
Scenedesmus
Phacus
Euglena
Unidentified Volvocales and Chlorococcales Six days after treatment, the green algae had been somewhat stimulated. Rhizochrysis, a yellow-green alga, was completely absent.

The second experiment was performed on sewage that had a dense bloom of blue-green algae; Microcystis and Oscillatoria were present at 2.6 × 10⁶ cells/liter. Ten days after treatment aeration was stopped and cell debris was allowed to settle. The results are shown below:

| | |
|---|---|
| 0 | 2.6 × 10⁶ cells/liter |
| 2.5 ppm | 8.3 × 10⁵ cells/liter |
| 5.0 ppm | 7.9 × 10⁵ cells/liter |
| 10.0 ppm | 6.6 × 10⁵ cells/liter |
| 15.0 ppm | 4.4 × 10⁵ cells/liter |

Most of the suspended cells that were enumerated appeared dead as evidenced by a brown coloration, by disrupted colonies and by fragmented filaments.

Toxicity Tests

For any algaecide to be useful in aquaculture, it must be without harmful effects on fish populations in ponds to be treated. Experiments to determine the effects of potassium ricinoleate on fish were performed in two 250 gallon aquaria using various concentrations of the algaecide. Batches of 25 live 5 in. catfish fingerlings were treated with 5, 10, 15, 20, 30, 35 and 100 ppm algaecide and observed for 48 hours. All fish survived concentrations of 35 ppm and lower. All fish had died at 12 hours at 100 ppm of the algaecide.

An additional experiment was conducted on live bluegill fingerlings at 5, 10, 15, 20, 30 and 35 ppm of the algaecide. All bluegills survived these concentrations.

Tests have also indicated that the present invention is effective in controlling the salt water organism commonly known as the "red tide", Gymnodinium, a dinoflaggelate.

It will be understood that the above description and examples are not to be considered as limiting the invention and that numerous departures may be made from the above without departing from the spirit and scope of the invention.

INDUSTRIAL APPLICABILITY

This invention is directed to the industry of control of algae in ponds, sewage lagoons, cooling towers, lakes, and other bodies of water, including managed bodies of water, and deals particularly with the use of certain long-chain fatty acids and salts thereof for chemical control of Cyanochloronta (blue-green algae). Stimulation of Chlorophycophyta (green algae) is achieved by the use of one embodiment of this invention.

What is claimed is:

1. A method of selectively controlling the growth of blue-green algae and yellow-green algae while maintaining a desirable balance of planktonic organisms in bodies of water in which populations of harmful blue-green algae are reduced in numbers leaving green algae and their oxygen producing capacity and food value substantially unreduced comprising adding from about 0.01 to about 100 ppm of a fatty acid compound selected from the group consisting of 9, 10-dihydroxystearic acid, Dodecanoic acid, Linoleic acid and Ricinoleic acid to the aqueous medium.

2. The method of claim 1 wherein said fatty acid is in the form of a water soluble salt.

3. The method of claim 2 wherein said water soluble salt is selected from the group consisting of sodium salts and potassium salts.

4. The method of claim 1 wherein the fatty acid is 9,10-dihydroxystearic acid.

5. The method of claim 1 wherein the fatty acid is linoleic acid.

6. The method of claim 1 the fatty acid is dodecanoic acid.

7. The method of claim 1 wherein the fatty acid is ricinoleic acid.

8. The method of claim 1 wherein the fatty acid is added to the aqueous medium in an amount of from about 0.1 to about 10 ppm.

9. A method of substantially eliminating blue-green algae from sewage lagoons comprising adding from about 0.01 to about 100 ppm of a fatty acid compound selected from the group consisting of 9, 10-Dihydroxystearic acid Dodecanoic acid, Linoleic acid and Ricinoleic acid to said sewage lagoon.

10. A method of maintaining a desirable balance of planktonic organisms in bodies of water comprising adding from about 0.01 to about 100 ppm of a fatty acid compound selected from the group consisting of 9, 10-Dihydroxystearic acid, Dodecanoic acid, Linoleic acid and Ricinoleic acid to said body of water.

* * * * *